United States Patent
Shen et al.

(10) Patent No.: US 9,733,336 B2
(45) Date of Patent: Aug. 15, 2017

(54) SYSTEM FOR LOCAL ERROR COMPENSATION IN ELECTROMAGNETIC TRACKING SYSTEMS

(75) Inventors: Eric Shen, Croton on Hudson, NY (US); Jochen Kruecker, Washington, DC (US)

(73) Assignee: Koninklijke Philips N.V., Eindhoven (NL)

( * ) Notice: Subject to any disclaimer, the term of this patent is extended or adjusted under 35 U.S.C. 154(b) by 1174 days.

(21) Appl. No.: 12/293,628

(22) PCT Filed: Mar. 22, 2007

(86) PCT No.: PCT/IB2007/051010
§ 371 (c)(1),
(2), (4) Date: Sep. 19, 2008

(87) PCT Pub. No.: WO2007/113719
PCT Pub. Date: Oct. 11, 2007

(65) Prior Publication Data
US 2010/0168556 A1    Jul. 1, 2010

Related U.S. Application Data

(60) Provisional application No. 60/788,472, filed on Mar. 31, 2006.

(51) Int. Cl.
*G01S 5/02* (2010.01)
*A61B 5/06* (2006.01)
(Continued)

(52) U.S. Cl.
CPC .............. *G01S 5/021* (2013.01); *A61B 5/062* (2013.01); *A61B 34/20* (2016.02); *A61B 90/36* (2016.02);
(Continued)

(58) Field of Classification Search
USPC ....... 600/310, 407, 409, 415, 422, 423, 424, 600/431, 473, 476; 324/207.17, 207.12
See application file for complete search history.

(56) References Cited

U.S. PATENT DOCUMENTS

| | | |
|---|---|---|
| 5,676,673 A | 10/1997 | Ferre et al. |
| 5,744,953 A | 4/1998 | Hansen |

(Continued)

FOREIGN PATENT DOCUMENTS

| | | |
|---|---|---|
| JP | 19930080893 A | 10/1994 |
| JP | 2001201316 A | 7/2001 |

(Continued)

*Primary Examiner* — Amanda Lauritzen Moher
*Assistant Examiner* — Shahdeep Mohammed

(57) ABSTRACT

A system for local metal distortion correction for using an accurate electromagnetic tracking system in a medical environment comprises an electromagnetic field generator monitoring a medical device having a suitable sensor coil. A correction function, derived from an error correction tool, is applied to the position and orientation readings of the sensor coil. The error correction tool comprises a number of electromagnetic sensors arranged in a fixed and known geometric configuration and is placed surrounding the site of the medical procedure. Sensor data is displayed on an imaging system. In addition, a distortion mapping can be done utilizing optical sensors for relative positioning readings along with an electromagnetic tracking system sensor.

12 Claims, 3 Drawing Sheets

(51) Int. Cl.
  *A61B 90/00* (2016.01)
  *A61B 34/20* (2016.01)
(52) U.S. Cl.
  CPC ............... *A61B 2034/2051* (2016.02); *A61B 2034/2055* (2016.02); *A61B 2090/0818* (2016.02); *A61B 2090/3975* (2016.02)

(56) References Cited

U.S. PATENT DOCUMENTS

| | | | | |
|---|---|---|---|---|
| 5,831,260 | A * | 11/1998 | Hansen | 250/221 |
| 6,235,038 | B1 * | 5/2001 | Hunter et al. | 606/130 |
| 6,261,247 | B1 | 7/2001 | Ishikawa et al. | |
| 6,288,785 | B1 * | 9/2001 | Frantz | A61B 5/06 250/559.29 |
| 6,400,139 | B1 | 6/2002 | Khalfin et al. | |
| 6,402,762 | B2 * | 6/2002 | Hunter et al. | 606/130 |
| 6,977,504 | B2 * | 12/2005 | Wright et al. | 324/326 |
| 7,835,778 | B2 * | 11/2010 | Foley et al. | 600/407 |
| 7,835,785 | B2 * | 11/2010 | Scully et al. | 600/424 |
| 8,180,430 | B2 | 5/2012 | Govari et al. | |
| 8,549,732 | B2 | 10/2013 | Burg et al. | |
| 2002/0068862 | A1 * | 6/2002 | Kleiman et al. | 600/407 |
| 2003/0163037 | A1 * | 8/2003 | Bladen et al. | 600/424 |
| 2004/0015075 | A1 * | 1/2004 | Kimchy et al. | 600/424 |
| 2005/0085720 | A1 * | 4/2005 | Jascob et al. | 600/424 |
| 2006/0036162 | A1 * | 2/2006 | Shahidi et al. | 600/424 |
| 2006/0241394 | A1 * | 10/2006 | Govari et al. | 600/423 |
| 2007/0038063 | A1 * | 2/2007 | Kuth et al. | 600/407 |
| 2007/0066887 | A1 * | 3/2007 | Mire et al. | 600/424 |

FOREIGN PATENT DOCUMENTS

| | | |
|---|---|---|
| JP | 2003513284 A | 4/2003 |
| JP | 2004101273 A | 4/2004 |
| JP | 2006285043 | 10/2006 |
| WO | WO0163312 A1 | 8/2001 |

* cited by examiner

SYSTEM FOR LOCAL ERROR COMPENSATION IN ELECTROMAGNETIC TRACKING SYSTEMS

CROSS REFERENCE TO RELATED CASES

Applicants claim the benefit of International Application Number PCT/IB2007/051010, filed Mar. 22, 2007, and Provisional Application Ser. No. 60/788,472, filed Mar. 31, 2006.

TECHNICAL FIELD

The present disclosure relates to an electromagnetic tracking system (EMTS) for medical devices and, more particularly, to metal distortion error compensation systems and methods for accurate tracking in a medical environment.

BACKGROUND

The outcomes of minimally invasive medical procedures can be improved by using electromagnetic tracking systems (EMTS) to track the location of medical instruments and display this information on medical images, thereby helping to guide the medical instrument to a target location in the anatomy. EMTS generally uses an electromagnetic field generator to create a local electromagnetic field at the site of the procedure and a medical instrument or device containing a suitable sensor coil. Electrical current is induced in the sensor coil which is a function of the position and orientation of the sensor coil relative to the electromagnetic field generator. The EMTS computes the position of the sensor coil, and therefore the position of the medical instrument, based on the induced electrical current. A particular advantage of EMTS is that line of sight is not required to determine/monitor instrument location or movement, thereby making it particularly suitable for tracking needles or catheters inside anatomy.

One of the main problems with using EMTS in a medical environment is the presence of metallic conductive or ferromagnetic objects in proximity to the electromagnetic field. These objects create distortions, or metal artifacts, which create errors in the position and orientation tracking of medical instrument(s). The table or platform capable of sustaining a medical procedure is usually a main source of metal distortions. However, other objects, such as CT gantry, X-ray or C-arm, can also cause and/or contribute to distortions. Such distortions and associated errors in a clinician's assessment/understanding of instrument positioning may directly and negatively affect the outcome of a medical procedure using EMTS. Currently the clinical utility of EMTS is limited because the positional and orientational accuracy of EMTS cannot be guaranteed in the presence of metal distortions.

U.S. Pat. No. 6,400,139 to Khalfin et al. discloses methods/apparatus for electromagnetic position and orientation tracking with distortion compensation functionality. More particularly, the Khalfin '139 patent discloses methods/apparatus that employ at least one stationary sensor, called a "witness sensor," having a fixed position and orientation near or within the volume to account for electromagnetic distortion. One or more probe sensors are placed on an object to be tracked within the volume, and the output of each witness sensor is used to compute the parameters of a non-real effective electromagnetic source. The parameters of the effective source are used as inputs to the computation of position and orientation as measured by each probe sensor, as if the object were in the non-distorted electromagnetic field produced by the effective source or sources.

Despite efforts to date, a need remains for systems and methods that effectively compensate for metal distortions, thereby improving the accuracy and/or reliability of EMTS in a medical/clinical environment. In addition, a need remains for systems/methods that improve EMTS performance such that catheter tracking in cardiac and vascular applications, oncology applications such as needle biopsies, radio-frequency ablations, cryoablations, prostate cancer therapies, etc., are effectively and reliably achieved. These and other needs are satisfied by the systems and methods disclosed herein.

SUMMARY

The present disclosure is directed to error compensation systems and apparatus for addressing metal distortions that exist and/or are encountered in using an electromagnetic tracking system (EMTS), e.g., in medical and/or surgical procedures. According to an exemplary embodiment, the disclosed EMTS includes an electromagnetic field generator that is adapted to generate an electromagnetic field. The electromagnetic field generator is generally adapted to be positioned in a medical/surgical/clinical environment, such that the electromagnetic field generated thereby may be used to track sensor data from electromagnetic sensors and suitable electromagnetic sensor coil(s). The disclosed sensor coil(s) are typically embedded in a medical device or other structure/element to be introduced to the clinical environment, thereby allowing positional and orientational data to be tracked while the medical device or other structure is positioned, in whole or in part, within an anatomy. An error compensation function is generated from an error compensation tool associated with the disclosed system/method, and error compensation generated thereby is applied to the positional and orientational data associated with the medical device or other structure for accurate tracking. The error-compensated information may be displayed on an imaging system, stored in computer memory and/or printed.

According to exemplary embodiments of the present disclosure, the disclosed error correction tool includes a plurality of electromagnetic sensors fixed in a known/predetermined geometric configuration. Preferably, the error correction tool is situated or oriented so as to surround the local area of interest, i.e., the clinical/anatomical region where a medical, surgical and/or diagnostic procedure is to take place. In a preferred embodiment, an optical tracking sensor is attached to the error correction tool for higher accuracy. The optical tracking sensor is generally unaffected by metal distortion and its position and orientation is fixed and known with respect to at least one electromagnetic sensor on the error correction tool.

In a further exemplary embodiment of the present disclosure, prior art EMTS-related problems are overcome by generating distortion mapping that allows for free movement of the generator and/or table. This embodiment utilizes an optical tracking system that is adapted to track position data from optical sensors placed on the electromagnetic field generator and table used in the medical/surgical procedure. A positioning system is used to move an EMTS sensor to different locations to facilitate mapping of distortion data. This creates several possible distortion maps for different positions of the table and field generator relative to each other. Thus, a single comprehensive mapping is obtained and, according to the present disclosure, subsequent movements of the table and/or field generator during and/or in between procedures does not negatively effect the reliability and/or accuracy of the disclosed EMTS. Indeed, according to exemplary embodiments of the present disclosure, an imaging system is provided that is adapted to display tracking information for a medical device or other structure that is advantageously compensated by distortion mapping.

Additional features, functions and advantages associated with the disclosed systems and methods will be apparent from the description which follows, particularly when read in conjunction with the figures appended hereto.

BRIEF DESCRIPTION OF THE DRAWINGS

To assist those of ordinary skill in making and using the disclosed systems and methods, reference is made to the appended figures, wherein.

DETAILED DESCRIPTION OF EXEMPLARY EMBODIMENT(S)

The present disclosure provides advantageous electromagnetic tracking systems (EMTS) for medical devices and other structures. The disclosed systems/methods provide metal distortion error compensation, thereby facilitating accurate tracking of such devices/structures in a medical/surgical environment. By effectively compensating for metal distortions, the disclosed systems and methods improve the accuracy and/or reliability of EMTS in a medical/clinical environment. For example, improved EMTS performance is provided such that effective and reliable catheter tracking in cardiac and vascular applications, oncology applications such as needle biopsies, radio-frequency ablations, cryoablations, prostate cancer therapies, and the like.

Figure 1:
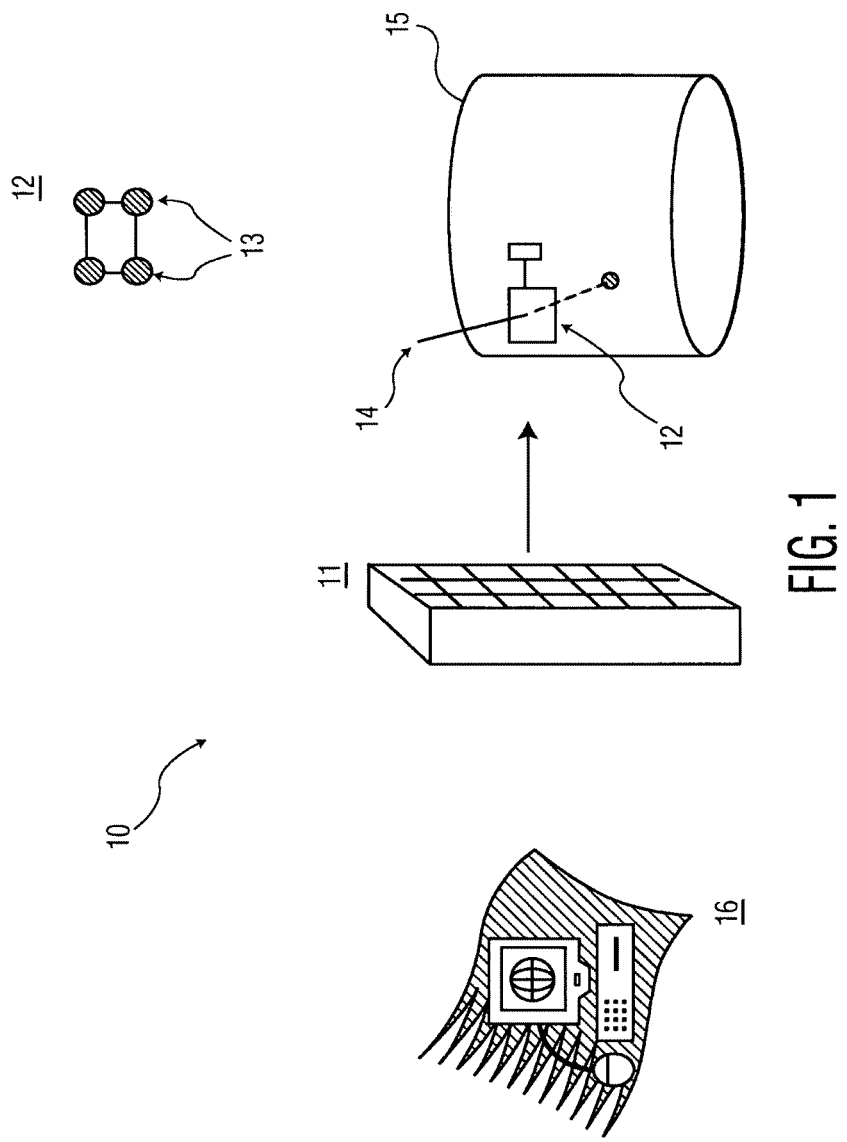
FIG. 1 is a schematic illustrating a first exemplary embodiment of the present disclosure.

Referring initially to FIG. 1, illustrated is electromagnetic tracking system (EMTS) 10 having an electromagnetic field generator 11. In a first embodiment, generator 11 creates a local electromagnetic field capable of tracking sensor data from electromagnetic sensors 13 and medical device 14. During a medical/surgical procedure, device 14 typically penetrates an anatomy 15 beneath the skin to a target location. An electromagnetic sensor coil is embedded on device 14. An electric current is induced in the sensor coil which is a function of position and orientation of the sensor coil relative to electromagnetic field generator 11. The sensor coil is detected by the local electromagnetic field generated by generator 11. Sensor data from the sensor coil is displayed on imaging system 16. Imaging system 16 can include, but is not limited to, a monitor with computer typical in a medical environment. This data consists of position and orientation of the sensor coil, thus the position and orientation of the medical device 14 can be determined. The medical device can be a needle, a catheter, or any device moving through an anatomy.

Error correction tool 12, having electromagnetic sensors 13, is placed surrounding the site of interest, typically over the location of the medical procedure. By monitoring position readings of sensors 13 on correction tool 12, a correction function is derived and applied to the sensor coil position and orientation data. The correction tool thus achieves local error compensation for metal distortions existing in the environment. These distortions are common among CT, X-ray and ultrasound environments.

Error correction tool 12 typically has a number of electromagnetic sensors arranged in a fixed and known geometric configuration. FIG. 1, for example, shows four sensors arranged in a square configuration. In an exemplary embodiment, the electromagnetic sensors could be arranged in a 10 cm by 10 cm square. In an alternative exemplary configuration, only three sensors are arranged in a triangle of known dimensions. In a preferred embodiment, the exact positions of the sensors relative to each other should be known. It is particularly useful to arrange the sensors in a way such that the site of interest for the procedure can be surrounded by the sensors.

According to exemplary embodiments of the disclosed systems and methods, positional readings are taken from sensors 13 when tool 12 is placed in the field of view of generator 11. If metal distortions are present (and absent correction functionality as disclosed herein), the position of one or more of the sensors will be incorrect and EMTS 10 will not properly recognize/translate the geometric arrangement. However, since the relative positions of sensors 13 are fixed and known according to the present disclosure, the disclosed systems and methods facilitate correction of the EMTS reading (i.e., un-distortion), thereby yielding the correct geometric shape. This correction can then be applied to the positional reading of medical device 14 and, in this way, the field local to the tool is compensated for errors caused by metal distortion.

Figure 2:
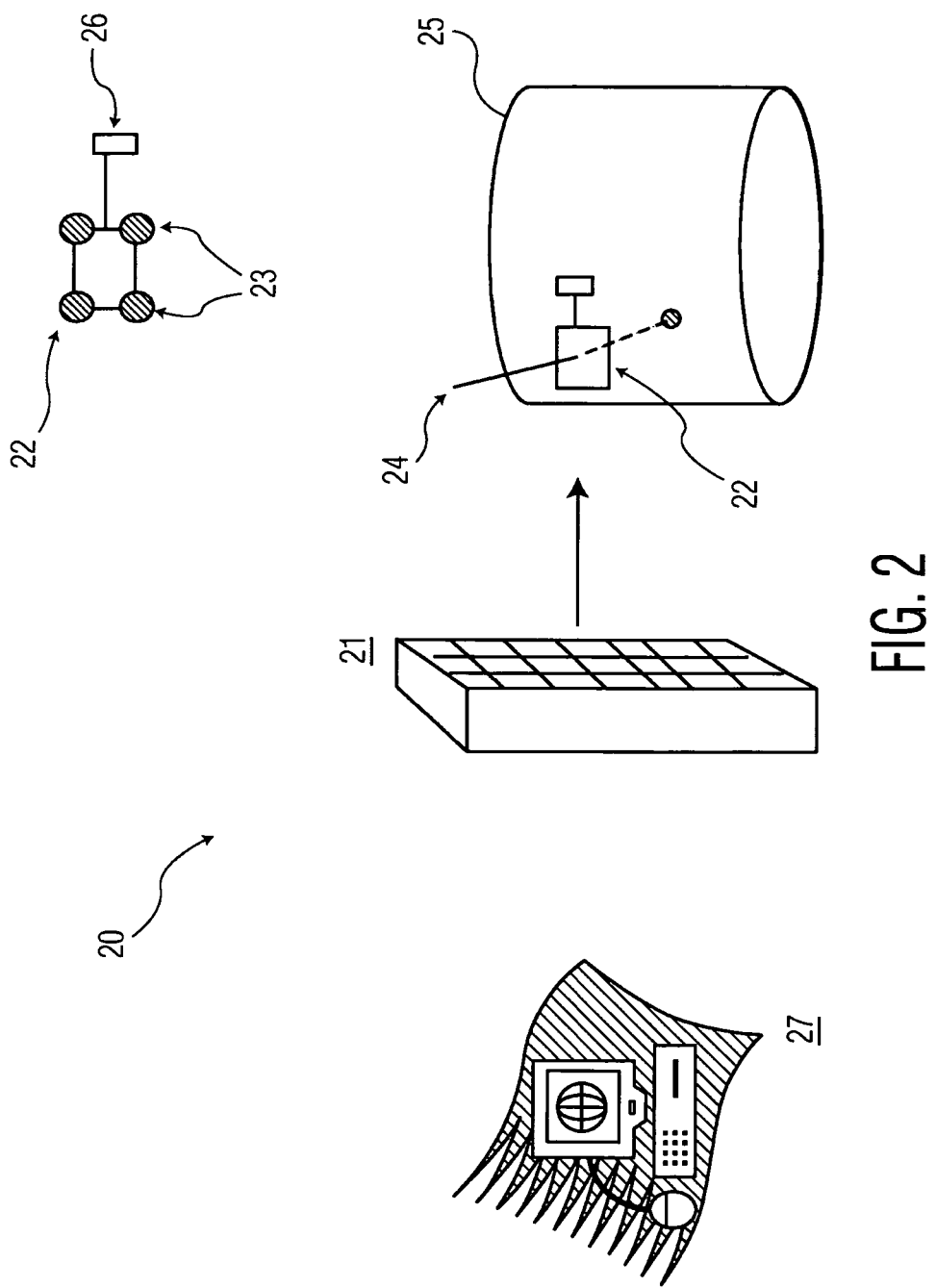
FIG. 2 is a schematic illustrating a second exemplary embodiment of the present disclosure.

Although it is possible to perform error correction solely using electromagnetic sensors, error may still exist since the absolute positions of the sensors read by the EMTS are not known in the presence of metal distortions. In a preferred embodiment of the present disclosure, means for identifying the absolute position of at least one of the sensors enables the absolute position of all sensors 23 to be known/determined. FIG. 2 illustrates an exemplary embodiment where optical tracking sensor 26 is attached to error correction tool 22. Optical tracking sensor 26 is generally in a fixed and known position relative to at least one of electromagnetic sensors 23. Optical tracking space and electromagnetic tracking space can be registered to imaging system 27, thus providing an absolute positional reference for error tool 22. Imaging system 27 can include, but is not limited to, a monitor with computer/central processing unit, as are known for use in a medical/surgical environment. In this preferred embodiment, absolute positions of electromagnetic sensors 23 generate a more accurate distortion correction function local to the error tool.

According to FIG. 2, EMTS 20 is schematically illustrated and includes an electromagnetic field generator 21. In this exemplary embodiment, generator 21 creates a local electromagnetic field capable of tracking sensor data from electromagnetic sensors 23 and medical device 24. During a medical/surgical procedure, device 24 typically penetrates an anatomy 25 beneath the skin to a target location. An electromagnetic sensor coil is embedded on device 24. An electric current is induced in the sensor coil which is a function of position and orientation of the sensor coil relative to electromagnetic field generator 21. The sensor coil is detected by the local electromagnetic field generated by generator 21. Sensor data from the sensor coil is displayed on imaging system 27. This data consists of position and orientation of the sensor coil, thus the position and orientation of medical device 24. The medical device can be a needle, a catheter, or any device moving through an anatomy.

Error correction tool 22, which includes electromagnetic sensors 23, is placed surrounding the site of interest, typically over the location of the medical procedure. By monitoring position readings of sensors 23 on correction tool 22, a correction function is derived and applied to the sensor coil position and orientation data, thereby achieving local error compensation for metal distortions existing in the environment. These distortions are common among CT, X-ray and ultrasound environments.

Error correction tool 22 typically has a number of electromagnetic sensors arranged in a fixed and known geometric configuration. FIG. 2, for example, shows four sensors arranged in a square configuration. As noted with reference to the embodiment of FIG. 1, the sensors may be arranged in a 10 cm by 10 cm square. In an alternative embodiment, only three sensors are arranged in a triangle of known dimensions. In a preferred embodiment, the exact positions of the sensors relative to each other are known. It is particularly useful to arrange the sensors in a way such that the site of interest for the procedure can be surrounded by the sensors.

Positional readings can be taken from sensors 23 when tool 22 is placed in the field of view of generator 21. If metal distortions are present, the position of one or more of the sensors will be incorrect and EMTS 20 will not properly translate the geometric arrangement. Since the relative positions of sensors 23 are fixed and known, it is possible to un-distort and correct the EMTS reading, thereby yielding the correct geometric shape. This correction can then be applied to the position reading of medical device 24 and, in this way, the field local to the tool is compensated for errors caused by metal distortion.

Figure 3:
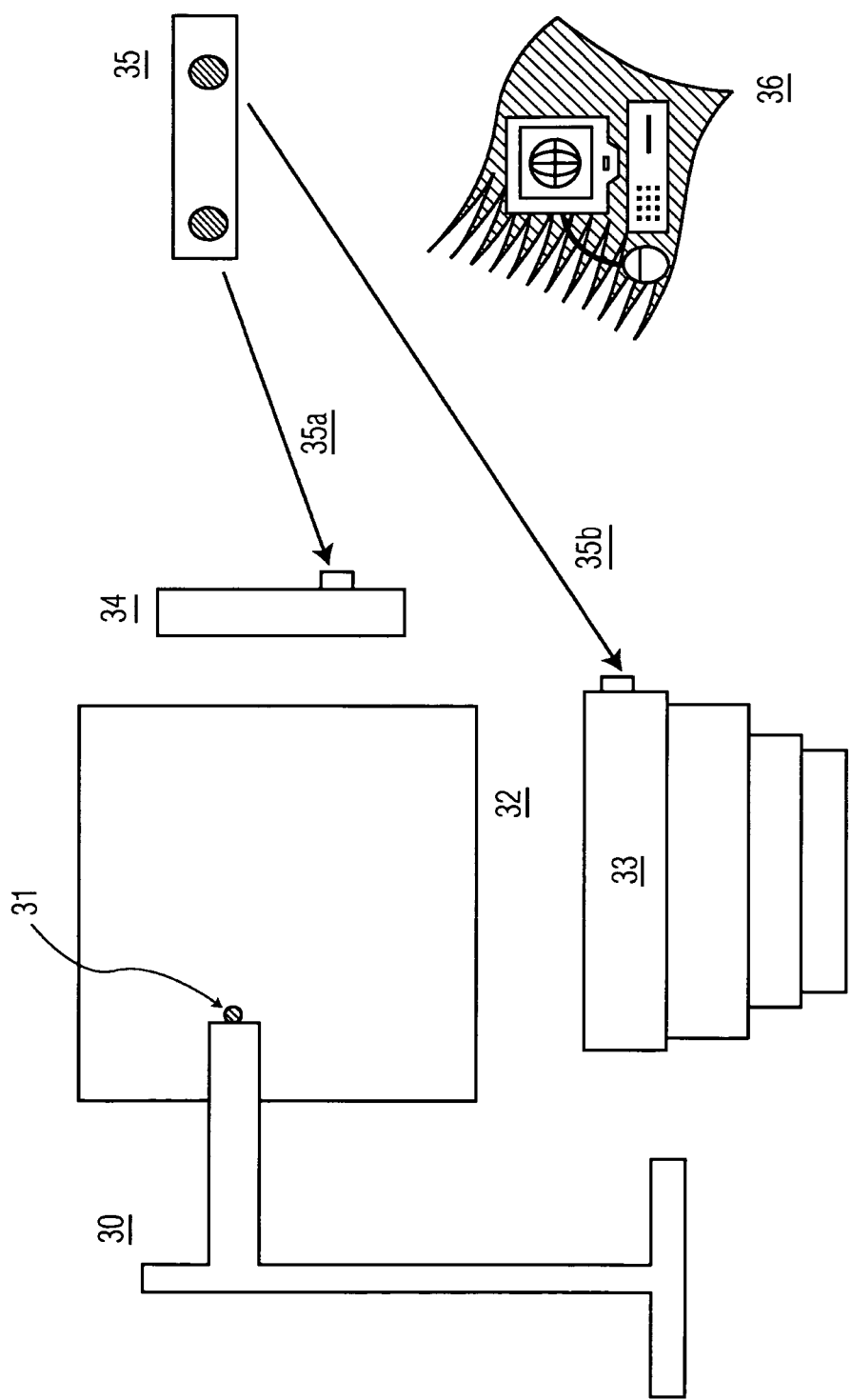
FIG. 3 is a schematic illustrating a third exemplary embodiment of the present disclosure.

FIG. 3 illustrates a third exemplary embodiment of the present disclosure in which electromagnetic field generator 34 has at least a first optical tracking sensor 35a. Generator 34 creates a local electromagnetic field capable of tracking sensor data from an electromagnetic sensor coil embedded on a medical device or other structure/element. An electric current is induced in the sensor coil. The electric current is a function of position and orientation of the sensor coil relative to electromagnetic field generator 34. Sensor data from the sensor coil is displayed on imaging system 36. Imaging system 36 can include, but is not limited to, a monitor with a conventional computer/central processing unit, as are typical in the medical/surgical environment. This data consists of position and orientation of the sensor coil, which translates to the position and orientation of the medical device. The medical device can be a needle, a catheter, or any device moving through an anatomy.

With further reference to FIG. 3, exemplary table 33 can take the form of a typical platform used for medical/surgical procedures, including but not limited to a CT table, X-ray table, or ultrasound table. As noted previously, the medical procedure environment, including table 33, typically creates metal distortions that alter the accuracy of a conventional EMTS. These distortions are advantageously overcome according to the exemplary embodiment of FIG. 3.

As schematically depicted in FIG. 3, at least a second optical tracking sensor is advantageously attached to table 33. Electromagnetic mapping is achieved through the use of positioning system 30 having an EMTS sensor 31. In the exemplary embodiment of FIG. 3, positioning system 30 is moved to different locations within a desired spatial volume, wherein electromagnetic sensor 31, first optical sensor 35a and second optical sensor 35b are in communication. Positioning data is gathered for all three sensors relative to each other, thereby permitting and/or facilitating mapping any local distortions caused by the local environment relative to different known positions of the positioning system, the electromagnetic field generator and the table.

Useful and practical distortion compensation is derived according to exemplary embodiments of the present disclosure by moving at least one sensor 31 to known location(s) with high accuracy within a desired spatial volume. Multiple mappings may be performed for many different locations and orientations of electromagnetic field generator 34 and/or table 33. Optical tracking sensors 35a and 35b can be a typical six degree of freedom optical sensor immune to metal distortions. Thus, comprehensive mapping and compensation are derived for different generator and table positions. This procedure need only be undertaken once, thereby enhancing the ease of use of the disclosed EMTS systems, e.g., in a medical/surgical environment. Once completed, both the generator and the table can be moved around during an actual medical/surgical procedure and the compensation mapping will still be valid.

According to an exemplary embodiment of the present disclosure, an optical tracking system 35 monitors location of optical tracking sensors 35a and 35b so that their positions are known at all times during the mapping procedure. Positioning system 30 positions EMTS sensor 31 very accurately at known locations in space. The corresponding position and orientation data is recorded on the EMTS. The field generator is then moved to a different location relative to the table and the procedure is repeated. The field generator and table need not be moved to many different locations; a few locations may be sufficient to derive a mapping that can compensate for a range of positions of the generator and table. The table is the main source of metal distortions in the use of EMTS in medical applications, however other objects in a typical medical environment, such as CT gantry, X-ray or C-arm, can also cause distortions. This method can be applied to other anticipated sources of disruption.

By providing error compensation, the use of EMTS is more realistic and practical, in turn allowing many opportunities for integrating medical imaging with medical device tracking. The technology is generically applicable to most any situation where a physician needs to guide a medical device to a location within an anatomy.

Although the present disclosure is provided with reference to exemplary embodiments of the present systems and methods, the present disclosure is not limited to such exemplary embodiments. Rather, the systems and methods of the present disclosure may be modified, altered and/or enhanced without departing from the spirit or scope hereof, as will be readily apparent to persons of ordinary skill in the art based on the description herein. The present disclosure expressly encompasses such modifications, alterations and enhancements within the scope hereof.

What is claimed:

1. A method for local error compensation caused by metal distortions in using an Electromagnetic Tracking System (EMTS) comprising the acts of:
generating an electromagnetic field from at least one electromagnetic field generator;
monitoring a positional reading of a medical device in an anatomy using a current induced by the electromagnetic field in at least one electromagnetic sensor coil of the medical device;
monitoring position readings from at least three electromagnetic sensors of an error correction tool that surrounds a region of interest and is configured to monitor the metal distortions wherein said error correction tool is situated within proximity of said medical device to obtain a monitored geometric shape, wherein the at least three electromagnetic sensors are arranged in a known and fixed configuration forming a reference geometric shape, and wherein said error correcting tool includes at least one optical tracking sensor attached to said error correcting tool in a fixed known position relative to at least one electromagnetic sensor of the at least three electromagnetic sensors;

comparing the monitored geometric shape with the reference geometric shape to obtain a comparison result;

deriving a correction function from said comparison result, wherein the correction function translates the monitored geometric shape to yield a corrected monitored geometric shape that conforms to the reference geometric shape of the at least three electromagnetic sensors;

applying said corrective function to said positional reading of the medical device to compensate for said metal distortions and obtain a corrected positional reading indicating a corrected position of the medical device, wherein the at least one optical tracking sensor is configured to provide optical data in an optical tracking space and the position readings from at least three electromagnetic sensors are in an electromagnetic tracking space;

registering the optical tracking space and the electromagnetic tracking space to an imaging system configured to display images of the medical device in the anatomy; and obtaining absolute positions of the at least three electromagnetic sensors based on the registering act.

2. The method according to claim 1, wherein said error correction tool has at least four electromagnetic sensors.

3. The method according to claim 1, wherein said current is a function of the position and orientation of said at least one electromagnetic sensor coil relative to said electromagnetic field generator.

4. The method of claim 1, wherein the at least three electromagnetic sensors are arranged spaced apart from each other in a triangle or a square.

5. The method of claim 1, wherein the at least three electromagnetic sensors are arranged in one plane.

6. An electromagnetic tracking system (EMTS) for tracking a medical device through an anatomy comprising:

an electromagnetic field generator generating an electromagnetic field for inducing a current in a sensor coil of the medical device to generate a positional reading of the medical device;

an error correction tool surrounding a region of interest and comprising at least three electromagnetic sensors arranged in a known configuration forming a reference geometric shape, wherein said error correcting tool includes at least one optical tracking sensor attached to said error correcting tool in a fixed known position relative to at least one electromagnetic sensor of the at least three electromagnetic sensors; and a processor configured to:

monitor position readings from the at least three electromagnetic sensors to obtain a monitored geometric shape of the at least three electromagnetic sensors;

compare the monitored geometric shape with the reference geometric shape to obtain a comparison result;

generate an error correction function from the comparison result, wherein the correction function translates the monitored geometric shape to yield a corrected monitored geometric shape that conforms to the reference geometric shape;

apply the error correction function to the positional reading of the medical device to compensate for metal distortions and obtain a corrected positional reading indicating a corrected position of the medical device, wherein the at least one optical tracking sensor is configured to provide optical data in an optical tracking space and the position readings from at least three electromagnetic sensors are in an electromagnetic tracking space;

register the optical tracking space and the electromagnetic tracking space to an imaging system configured to display images of the medical device in the anatomy; and obtain absolute positions of the at least three electromagnetic sensors based on the registering act.

7. The EMTS of claim 6, wherein the at least three electromagnetic sensors are arranged spaced apart from each other in a triangle or a square.

8. The EMTS of claim 6, wherein the at least three electromagnetic sensors are arranged in one plane.

9. The EMTS according to claim 6, wherein the at least one optical tracking sensor is attached to said error correction tool in a fixed and known position relative to the sensor coil of the medical device.

10. The EMTS according to claim 9, wherein said optical tracking sensor and said sensor coil are registered to an imaging source for providing a position reference for said error correction tool.

11. The EMTS according to claim 9, wherein said error correction tool has at least four electromagnetic sensors.

12. The EMTS according to claim 9, wherein said current is a function of the position and orientation of said sensor coil relative to said electromagnetic field generator.

* * * * *